United States Patent [19]
Carr et al.

[11] Patent Number: 6,146,359
[45] Date of Patent: *Nov. 14, 2000

[54] APPARATUS FOR CONTROLLEDLY WARMING LOW FLOW RATE INFUSATES

[75] Inventors: Kenneth L. Carr, Harvard; James Regan, Waltham, both of Mass.

[73] Assignee: Microwave Medical Systems, Inc., Acton, Mass.

[*] Notice: This patent is subject to a terminal disclaimer.

[21] Appl. No.: 08/977,747

[22] Filed: Nov. 25, 1997

Related U.S. Application Data

[63] Continuation-in-part of application No. 08/524,392, Sep. 6, 1995, Pat. No. 5,690,614.

[51] Int. Cl.[7] ........................................................ A61F 7/12
[52] U.S. Cl. ............................................. 604/114; 219/687
[58] Field of Search .................................. 604/114, 113; 219/687–689

[56] References Cited

U.S. PATENT DOCUMENTS

| | | | |
|---|---|---|---|
| 4,680,445 | 7/1987 | Ogawa . | |
| 5,245,693 | 9/1993 | Ford et al. | 392/470 |
| 5,381,510 | 1/1995 | Ford et al. | 392/470 |
| 5,437,635 | 8/1995 | Fields et al. | 604/65 |
| 5,690,614 | 11/1997 | Carr et al. | 604/114 |

FOREIGN PATENT DOCUMENTS

| | | |
|---|---|---|
| 0 296 777 | 12/1988 | European Pat. Off. . |
| 0 649 665 A1 | 4/1995 | European Pat. Off. . |

*Primary Examiner*—Mark Bockelman
*Attorney, Agent, or Firm*—Cesari and McKenna, LLP

[57] ABSTRACT

Infusate warming apparatus comprises a housing defining an internal cavity. A lossy asymmetric transmission line is situated in the housing which transmission line includes an elongated electrical conductor having opposite ends and a conduit for conducting infusate which is highly absorptive to electromagnetic energy of a first frequency through the housing in close proximity to the conductor. A connector extends into the housing for coupling an external electromagnetic signal of the first frequency to one end of the conductor so as to subject the infusate to an energy field which heats the infusate. A temperature sensor for sensing the infusate temperature and controlling the signal to maintain a constant infusate delivering temperature is also disclosed.

59 Claims, 5 Drawing Sheets

APPARATUS FOR CONTROLLEDLY WARMING LOW FLOW RATE INFUSATES

RELATED APPLICATION

This application is a continuation-in-part of Ser. No. 08/524,392 filed Sep. 6, 1995, now U.S. Pat. No. 5,690,614.

FIELD OF THE INVENTION

This invention relates in general to microwave warming apparatus for blood and intravenously fed fluids. It relates especially to such apparatus which can handle low fluid flow rates and also provide close control over the temperature of the fluid being warmed.

BACKGROUND OF THE INVENTION

In the medical field, there exists a number of applications requiring the warming of blood and intravenous (IV) fluids. For example, in connection with cardiac surgery during extracorporeal blood circulation, the patient is first cooled in order to slow metabolism and thereafter there is a requirement that the circulating blood be warmed. Another application is the warming of blood or intravenous fluids in a trauma situation. For example, heated IV fluids are useful in hypothermic patients and in trauma patients requiring massive IV resuscitation.

One common technique for warming blood is to pass the blood through coils immersed in a warm water bath. Microwave heating has also been employed in connection with the warming of blood and IV fluids. An example of an in-line microwave warmer for blood and IV fluids is described in U.S. Pat. No. 5,073,167. That apparatus is advantageous because it monitors the liquid temperature radiometrically and controls the heating power level based on the temperature measurements taken so that close control is maintained over the temperature of the fluid being warmed. Typically, the fluid exiting the warmer should have a temperature close to normal body temperature, i.e., 37° C.

However, the physical sizes of those prior warmers necessitates that they be supported on an IV pole relatively remote from the patient. Resultantly, the fluid exiting those conventional blood warmers immediately begins to cool to room temperature and this cooling increases as the rate of infusion slows and the length of the patient IV line increases. In many cases, the warm IV fluid may sit in the patient line, slowly dripping its way to the patient's IV site. The constant exposure of the fluid to room temperature, e.g., 20° C., steadily reduces the temperature of the fluid. In some cases, the problem is exacerbated because the volume of fluid infused at a low flow rate may be quite large relative to the size of the patient, particularly, in pediatric and neonate applications, causing a significant decrease in the patient's temperature.

In actuality, in the year 1989, blood transfusions of 1 to 2 units at flow rates less than 25 ml./min. accounted for more than 60% of the 3.2 million U.S. patients who received a total of 12.1 million units of red blood cells. Fluid exiting a typical warmer with a temperature of 37° C. at a flow rate of 100 ml./hour cooled to 24.4° C. after traveling through a typical length (105 cm) of patient IV tubing; see Faries G., Johnston C., Pruitt K. M., Plouff R. T.: "Temperature Relationship To Distance And Flow Rate Of Warmed IV Fluid", ANN EMERG MED 20: 1189–1200, 1991.

Relatively recently, a warmer has been developed to address low flow rate warming. The design uses a water jacket to surround the patient IV line. The water jacket, in turn, connects to a pole-mounted water bath maintained at a temperature of about 40° C. by a 300 watt heater and circulating pump. Thus, the device surrounds the patient line with a layer of circulating warm water all the way to the patient and thus substantially eliminates patient line cool down. However, that device is disadvantaged because the water jacketed tubing is relatively large in diameter and inflexible making it difficult to attach to the catheter which introduces the infusate into the patient and adding mechanical stress to the catheter connection at the infusion site. Because of this, it has been found necessary to add a short length of non-insulating IV tubing between the jacketed tubing and the catheter thereby further fostering the patient line cool down problem.

Also, there is always a risk associated with the use of warm water for heating because of the danger of infection. Bacteria grows rapidly in warm water, requiring great care to prevent contact between the warm water and the tubing interconnections during a warming procedure. Also, to ensure sterility, the warm water bath must be emptied and cleaned regularly to avoid possible contamination.

Another problem with prior warmers generally is that they have a relatively large residual or priming volume, e.g., 20 ml or more. This is an important consideration for at least two reasons. First, a blood warmer may be on an infant or small child during extracorporal blood circulation. A typical infant may have a total blood volume of only 40–50 ml. This means that during the blood warming process, a large percentage of the patient's blood is outside the body at any given time which could cause patient trauma. Secondly, sometimes the infusate being administered includes very expensive drugs. If the infusion line includes a warmer with a high residual volume, the large amount of drug that remains in the line after the patient receives his prescribed dosage must be thrown away at a loss or be recovered which is expensive. Another possibility is to infuse the patient with saline interrupted by a dose or window of drug. However, this requires close monitoring of the infusion process which is labor intensive.

Finally, the conventional blood warmers of which we are aware are relatively bulky and heavy devices which have a relatively large footprint. Therefore, they are difficult to move around and difficult to locate close to a patient to avoid the long tubing lines to and from the patient.

SUMMARY OF THE INVENTION

Accordingly, it is an object of the present invention to provide apparatus for controlledly warming blood and IV fluids rapidly and uniformly independent of changes in the fluid inlet temperature and flow rate.

Another object of the invention is to provide such apparatus which is quite small and compact so as to allow fluid warming in close proximity to the patient, dramatically reducing the length of the patient line between the warmer and the patient so that the fluid actually entering the patient has precisely the desired temperature.

Still another object of the invention is to provide warming apparatus which has a very small residual or priming volume.

A further object of the invention is to provide apparatus of this type which accurately controls the temperature of the fluid being warmed through the use of passive, non-invasive radiometric sensing.

A further object of the invention is to provide apparatus for warming blood and IV fluids which is portable for field or ambulance use.

Still another object of the invention is to provide such a warmer which includes safety provisions for insuring that the insert is properly seated in the heater device during operation of the warmer.

Yet another object of the invention is to provide such apparatus whose portion contacted by the fluid being warmed is fully disposable and relatively inexpensive to make.

A further object is to provide warming apparatus of this type whose disposable portion consists of a pouch-like plastic cell for routing the fluid through the warmer.

A further object is to provide a warmer of this type comprising a small clam shell-type heater/temperature sensor device for containing a disposable fluid carrier or cell that defines a flow path for the fluid being warmed.

Another object of the function is to provide a disposable plastic fluid carrier on call for a low flow rate fluid warmer.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, the apparatus comprises a small, in-line fluid warmer which may be connected to the patient IV line in close proximity to the infusion site at the patient, i.e., within a few inches. Basically, the warmer is a microwave integrated circuit comprising a housing defining a microwave heating cavity with electrically conductive walls and which is divided lengthwise by a cell support. Preferably, the housing is formed as a "clam shell" to provide ready access to the support for an inexpensive disposable fluid carrier or cell which defines the actual flow path through the warmer for the infusate being warmed.

The warmer also includes a center conductor in the heating cavity. In one warmer embodiment, the center conductor is printed on the cell support. In a second embodiment, the conductor is printed on a wall of the cell itself. In both embodiments, the infusate, which has a relatively high dielectric constant and is very absorptive at microwave frequencies, flows along the cell path through the heating cavity at one side of the support and forms the base material of the microwave integrated circuit. The volume of the cavity at the other side of the cell support is filled with air or other material which has a low dielectric constant so that substantially all of the lines of microwave energy will be confined to the portion of the cavity containing the infusate-filled disposable carrier or cell. Thus, the warmer is essentially a lossy asymmetric strip transmission line (microstrip) in which the fluid or blood in the disposable cell replaces the usual high dielectric/low loss ceramics used in common microstrip circuitry. However, unlike such ceramics, blood is very absorptive at microwave frequencies.

The warming apparatus also includes a solid state programmable transmitter for delivering microwave energy to the center conductor of the warmer and a sensor for sensing the temperature of the infusate leaving the warmer. The sensor may be a conventional thermocouple or thermister located near the fluid outlet end of the warmer with the temperature signal being taken out on the center conductor. More preferably, the apparatus includes provision for noninvasive radiometric temperature sensing of the fluid being warmed. In both cases, a diplexer may be used to separate the microwave heating frequency from the received temperature-indicating frequency, thus allowing the use of a common coaxial cable and connection to the center conductor of the warmer. This is important since it results in smaller size and fewer components which inevitably means that the apparatus has superior reliability and lower cost.

Preferably, the temperature signal is used to control the transmitter to maintain the fluid flowing to the patient at a desired constant value, e.g., 37° C.

When the apparatus is in operation, the transmission line comprised of the center conductor and the infusate in the carrier or cell is of sufficient length to attenuate the microwave energy from the transmitter so as to provide uniform heating along the transmission line. In other words, the lossy transmission line, unlike an antenna or transducer deposits power per unit length. It also provides a good match as seen at the input of the transmission line at the operating frequency of the transmitter.

The present warming apparatus is able to deliver infusate at a precisely controlled temperature e.g., 37° C., at fluid flow rates of 1 to over 100 ml./min. Since the heating cavity section of the apparatus can be located quite close to the patient, i.e., with a few inches, and the priming or residual volume of the carrier is quite small, i.e., 0.5–2 ml. between the warmer and the patient, the temperature of the fluid infused into the patient is substantially the same as the temperature of the fluid leaving the heating cavity. Thus, the apparatus can deliver fluids at normothermic temperatures even at low fluid flow rates. Therefore, the apparatus should prove to be quite useful for the prevention of hypothermia, particularly in small patients and neonates.

Yet, because the apparatus' disposable carrier is essentially a small plastic carrier or cell which is very inexpensive to manufacture in quantity, the overall apparatus is quite affordable. Therefore, the warming apparatus should find wide application particularly in hospitals and clinics for situations requiring the efficient and rapid warming of blood and other IV fluids.

Also, while the apparatus specifically described herein operates at microwave frequencies, it should be understood that certain aspects of the invention are also applicable to warmers which operate at lower, e.g., RF, frequencies.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENTS

Figure 1:
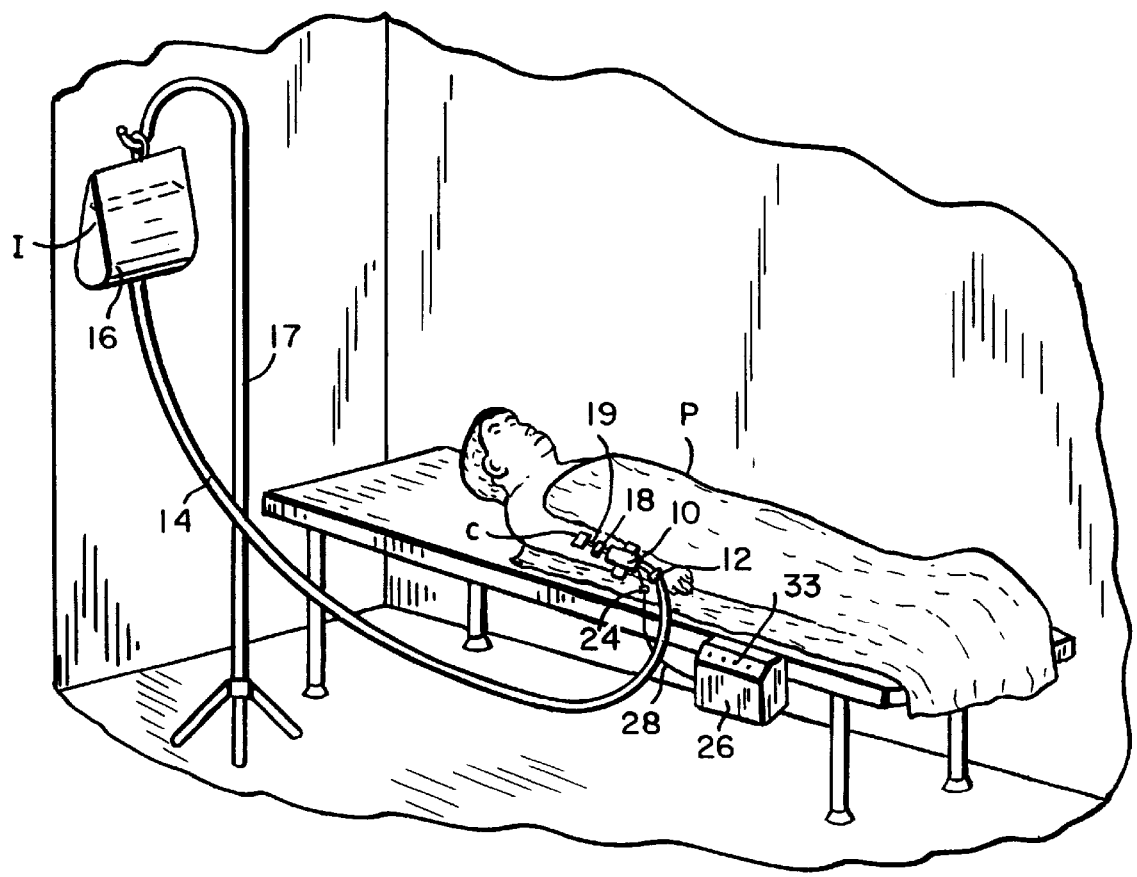
FIG. 1 is a diagrammatic view of microwave infusate warming apparatus embodying the invention.

Referring to FIG. 1 of the drawings, the warming apparatus includes an in-line, flow-through fluid warmer 10 having a fluid inlet fitting 12 adapted to be connected by an IV line 14 to an infusate source, e.g., a blood bag 16, containing an infusate I and supported on a pole stand 17 positioned next to the patient P being infused. The warmer 10 also has an outlet fitting 18 for connection by an IV line 19 to an infusate destination such as a transcutaneous catheter C in patient P. Fittings 12 and 18 may be standard Luer-lock connectors, for example. Warmer 10 may be secured to the patient P as shown or to his/her bedding close to the infusion site so that the fluid line 20 from the warmer to the patient may be as short as a couple of inches.

Figure 2:
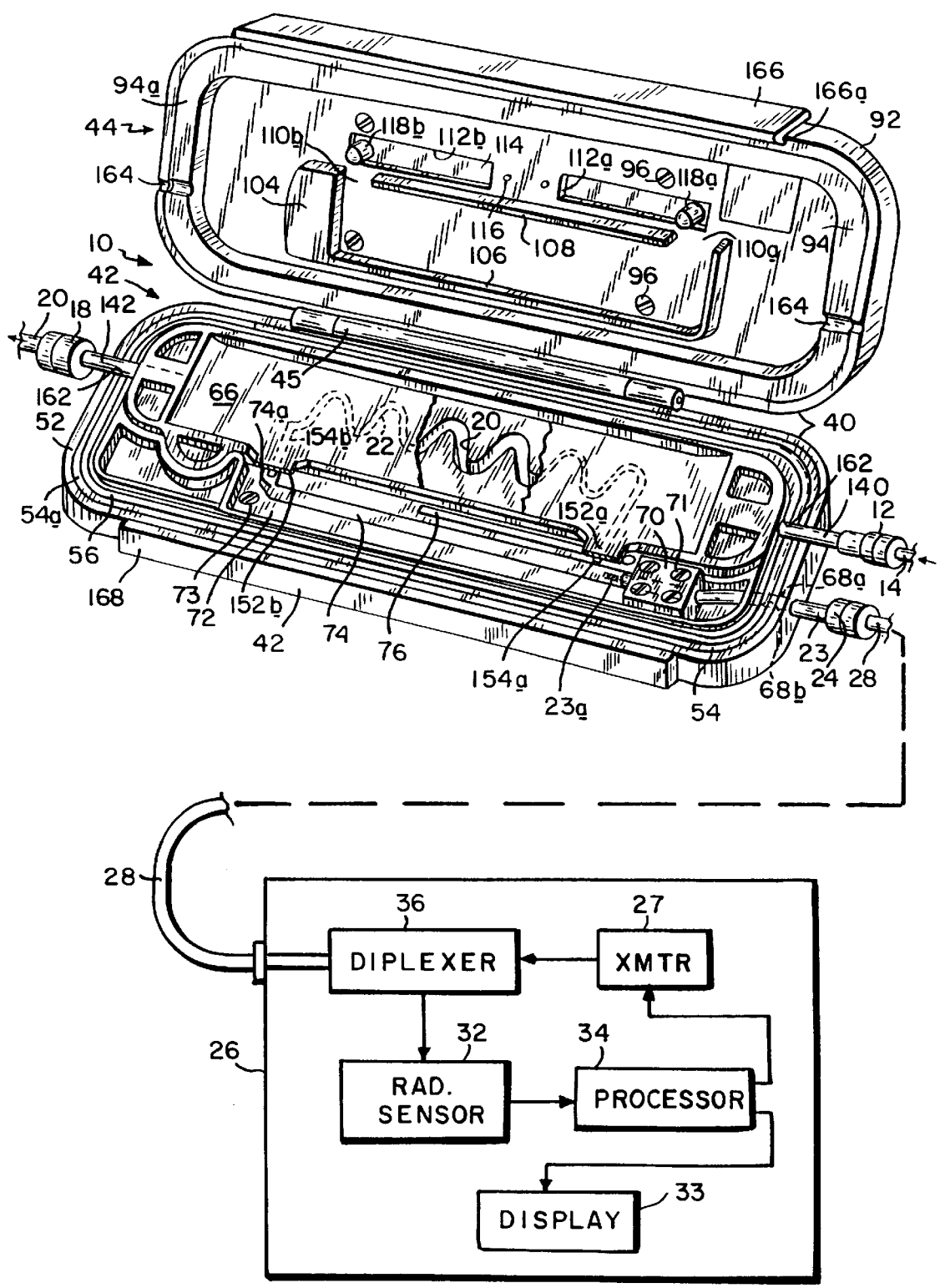
FIG. 2 is a perspective view on a larger scale, with some parts shown diagrammatically, of the FIG. 1 apparatus with the apparatus' warmer in the open position.

As shown in FIG. 2, the warmer 10 is actually a lossy transmission line comprising the infusate I flowing along a fluid path 20 in warmer 10 and a center conductor 22 adjacent path 20. The conductor 22 receives microwave energy via a single coaxial cable 23 terminated by a connector 24 from a transmitter/receiver 26 which is coupled to connector 24 by way of a cable 28. Unit 26 may be supported near the patient, but relatively remote from the infusion site.

The unit 26 includes a microwave transmitter 27 which delivers power via diplexer 36 and cable 28 to the conductor 22. The microwave energy coupled to the warmer 10 is attenuated by the infusate I flowing along path 20, which fluid is highly absorbent at the frequency of transmitter 26, e.g., 2450 MHz or, to minimize cable loss, 915 MHz. In the process, the infusate absorbs energy and becomes heated so that it leaves warmer 10 at an elevated temperature.

The apparatus also includes a radiometric sensor or radiometer 32 in unit 26. The radiometer is connected by way of diplexer 36 and cable 28 to the warmer's connector 24. Sensor 32 monitors the temperature of the infusate in warmer 10. Preferably, the sensor is responsive at a signal frequency much higher than the transmitter frequency, e.g., 4.0 GHz. The output of the sensor 32 is applied to a display 33 and to a processor 34 both of which are in unit 26. The processor controls the power output of the microwave transmitter 27 to maintain the temperature of the infusate leaving warmer 10 at a selected substantially constant value, e.g., a normal body temperature of 37° C.

The warmer 10, which requires only the one connector 24 and the one cable 28, can function in both transmitting and receiving modes because of the presence of the diplexer 36 in unit 26 which connects transmitter 27 and sensor 32 to cable 28. The basic details and operation of warmer 10 and transmitter/receiver unit 26 are described in the above application Ser. No. 08/524,393, the contents of which is hereby incorporated herein by reference.

Figure 3:
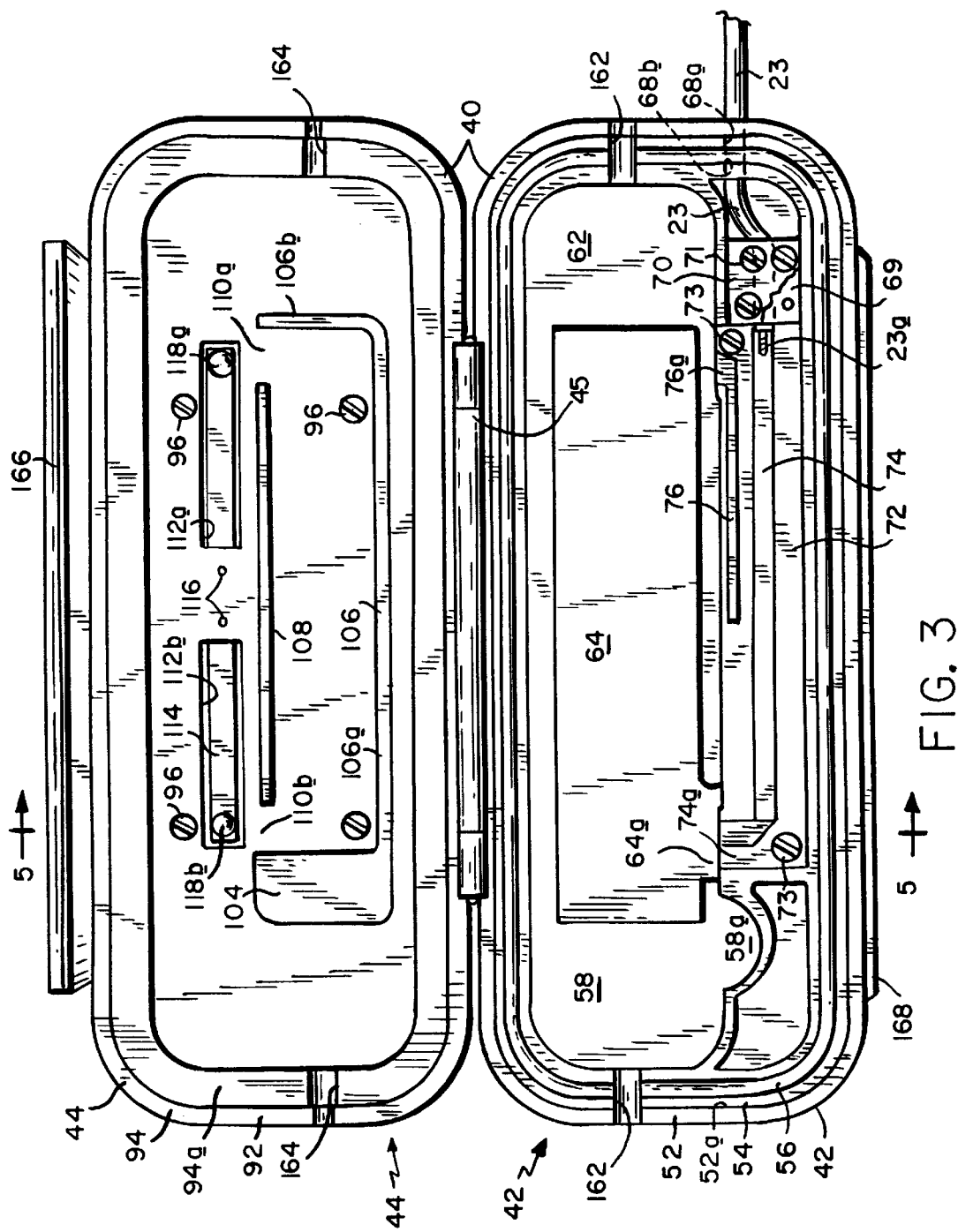
FIG. 3 is a plan view showing the open warmer of the apparatus in greater detail.

Referring now to FIGS. 2 and 3, the warmer 10 includes a relatively small, e.g. 5.5×2.3×1 in., housing 40, e.g., of aluminum metal or metallized plastic, so that at least its internal walls are electrically conductive. Preferably, the housing 40 is a clam shell-type housing having a base section 42 and a cover section 44. The two housing sections are connected together on edge by a hinge 45 so that they can move relatively between an open position shown in FIG. 2 and a closed position illustrated in FIGS. 1 and 5. When closed, the housing defines an internal cavity 46 (FIG. 5) and functions as a guided wave structure at the operating frequency of transmitter 26 to prevent radiation losses from the cavity.

Section 42 comprises an outer shell 52 of a suitable rugged impact-resistant plastic material such as polycarbonate. Positioned in the outer shell is a metal insert 54 which is grooved along its edge margin 54*a* to receive a string-like resilient seal 56 which extends parallel to the edge of the insert.

Insert 54 is relieved to form a pair of mirror image, generally D-shaped depressions 58 and 62 adjacent the opposite ends of insert 52 near the edge thereof adjacent to hinge 45. For reasons that will become apparent, depression 58 has a semi-circular extension 58*a* which extends away from hinge 45. As best seen in FIG. 3, the depressions 58, 58*a* and 62 are shaped to leave a relatively large raised rectangular pad 64 centered between the ends of insert 52. Pad 64 functions as a support for a disposable fluid carrier or cell 66 shown in FIGS. 2 and 4 to be described in more detail later. Suffice it to say at this point that cell 66 defines the fluid path 20 referred to above and may also include the center conductor 22.

As best seen in FIG. 3, the coaxial cable 23 extends into an end of housing section 42 through aligned holes 16*a* and 68*b* in shell 52 and insert 54, respectively. The cable extends across a raised pad 69 in insert 54 and the segment of the cable crossing pad 69 is stripped of its outer insulation so that the outer conductor of the cable makes electrical contact with pad 69. Also, the inner insulating layer at the end of the cable is stripped away to reveal the inner cable conductor 23*a* which projects beyond pad 69. The cable segment crossing pad 69 is clamped to the pad by a block 70 which is secured to pad 69 by threaded fasteners 71.

Extending alongside pad 64 beyond block 69 is an elongated printed circuit board 72 which is secured to insert 54 by threaded fasteners 73. Circuit board 72 carries a conductive stripe 74 which extends from a location underlying the exposed end of cable conductor 23*a* to which it is soldered to a location near the opposite end of pad 64 where the conductive stripe terminates in a side branch 74*a* which extends toward the pad. Pad 64 also has a sidebranch 64*a* which extends toward side branch 74*a*.

Circuit board 72 also carries a narrower conductive stripe 76 which extends parallel to stripe 74. Stripe 76 extends from a point mid-way along the circuit board toward the right in FIG. 3 to a location adjacent said opposite end of block 64 where it terminates in a side branch 76*a* which extends towards that block. As will be seen later, the paths of the side branches 74*a* and 76*a* are designed and located to make electrical contact with the opposite ends of conductor 22 in carrier 66.

Figure 5:
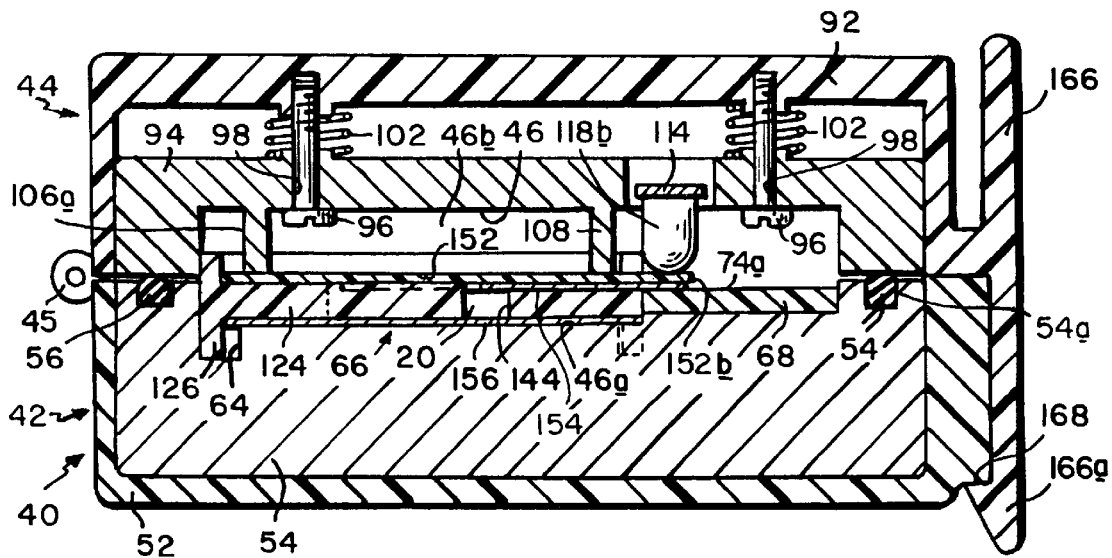
FIG. 5 is a sectional view taken along line 5—5 of FIG. 3 with the warmer closed and the FIG. 3 carrier mounted in the warmer.

Still referring to FIGS. 2 and 3, cover section 44 of housing 40 includes a molded plastic shell 92 having a metal insert 94 snugly positioned in the shell. Preferably the insert is resiliently mounted to the shell so that the insert is urged out of the shell. More particularly as best seen in FIG. 5, the insert 94 is secured to shell 92 by four machine screws 96 which extend through holes 98 in the insert and are screwed into the broad top wall of the shell 92. Coil springs 102 encircle the screws to bias the insert away from the top wall of the shell and to provide compliance for the insert when the cover 44 is moved to its closed position as shown in FIG. 5.

Still referring to FIGS. 2 and 3, insert 94 is provided with an edge margin 94*a* which is arranged to press against the seal 56 in section 42 when the cover is in its closed position as shown in FIG. 5. Inboard that margin 94*a*, the insert is relieved except for a relatively wide raised pad 104 adjacent to one end of pad 64 in base section 42 and a contiguous generally L-shaped rib 106 whose long leg 106*a* extends from pad 104 parallel to pad 64 almost to the opposite end of pad 64 where the rib turns to form the short leg 106*b* of the L which leg extends away from pad 64 a distance which is substantially equal to the width of pad 64. There is also a raised rib 108 spaced parallel to leg 106*a* and extending between pad 104 and the free end of the rib leg 106b. The pad 104 and ribs 106 and 108 are located in cover section 44 so that when the cover section is in its closed position shown in FIG. 5, pad 104 overlies one end segment of pad 64 in base section 42 while the ribs 106 and 108 overlie the edge margins of that pad 64.

It should be noted that the rib 108 is shorter than the leg 106a of rib 106 leaving gaps 110a and 110b between the opposite ends of rib 108 on the one hand, and pad 104 and rib leg 106b on the other for reasons that will become apparent.

A pair of aligned longitudinal slots 112a and 112b are formed in insert 94 adjacent to rib 108. These slots receive the opposite end segments of a leaf spring 114 which passes under the insert. The leaf spring is secured at its midpoint to the insert by fasteners 116 and the leaf spring is bent so that its opposite ends project out slightly from the slots 112a and 112b. Also, a pair of post 118a and 118b with rounded ends are mounted to the opposite ends of the spring 114. As will be seen, these spring-biased posts 118a and 118b are used to hold the carrier 66 in place when the housing 40 is in its closed position shown in FIG. 5.

Figure 4:
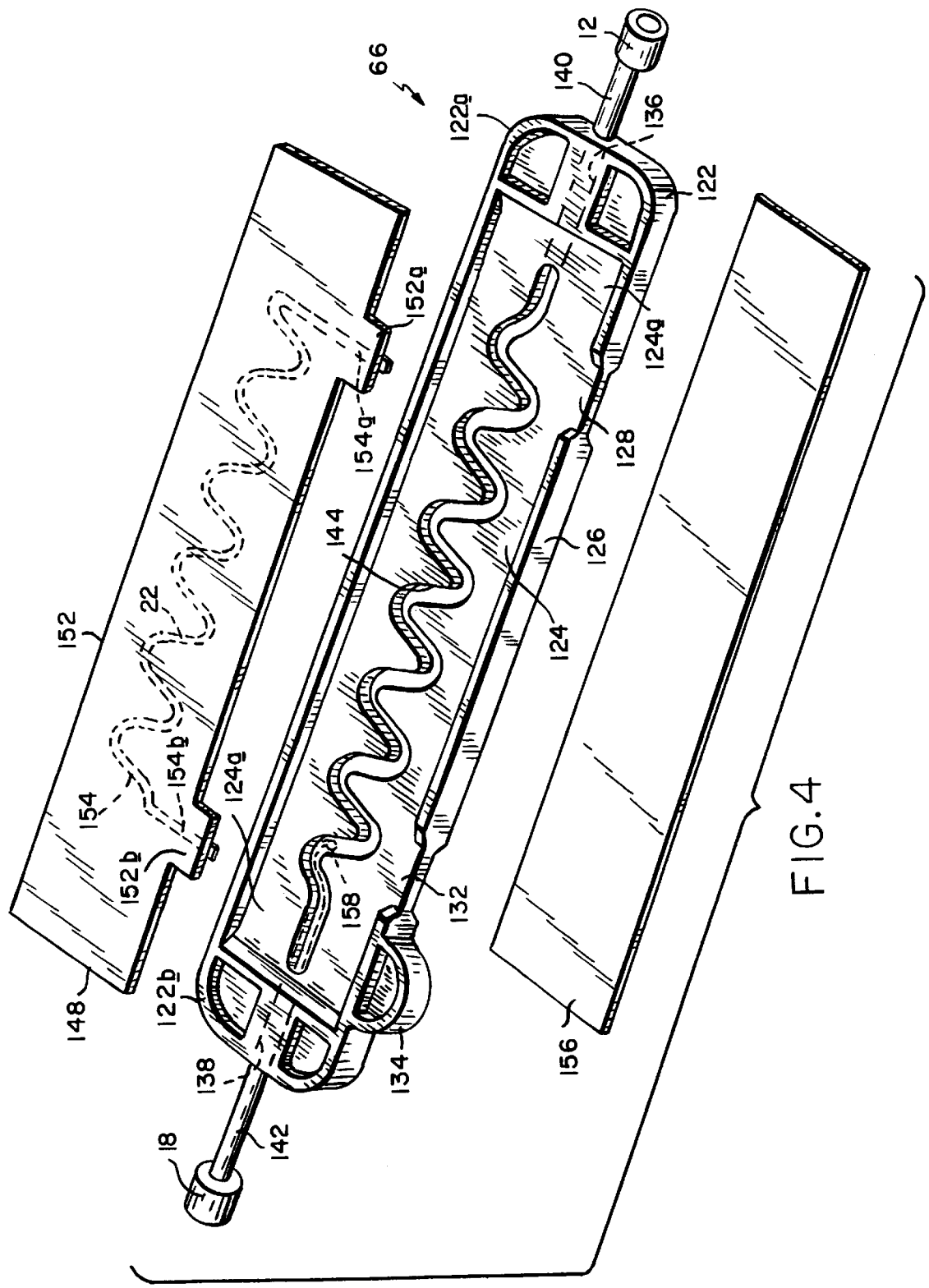
FIG. 4 is an exploded perspective view, on a still larger scale, of the fluid carrier used in the FIG. 3 warmer.

Refer now to FIGS. 4 and 5 which show the carrier 66 in detail. The carrier comprises an elongated generally rectangular rigid base 122 having a central plate 124 with a peripheral flange 126 which extends above and below the plate. The base is of plastic and therefor transparent to microwave energy. A pair of notches 128 and 132 are formed in the flange at one side of base 122 for reasons that will become apparent. Also, on that same side of the frame between notch 132 and the end of the frame is a key 134 which projects out laterally from the frame. When the carrier is positioned properly in the housing 40, this key seats in the extension 58a of depression 58 (FIG. 3) establishing the proper position, i.e., polarity, of the carrier in the base section 42.

The carrier base 122 has a pair of mirror image end extensions 122a and 122b with axial portions that are much thicker than plate 124 in which are formed a pair of collinear lengthwise passages 136 and 138. A plastic tube 140 leads from passage 136 to connector 12. A similar tube 142 extends from passage 138 to the connector 18.

Also formed in plate 124 is a through slot 144 which extends between passage 136 and 138 and communicates with those passages. The illustrated slot 144 meanders although it need not do so.

The second component of carrier 66 is a strip of printed circuit 148 which is shaped and dimension to cover and be adhered to plate 124. Circuit 148 includes a dielectric substrate 152 having a pair of side tabs 152a and 152b which are arranged to project into the notches 128 and 132, respectively, of base 122 when the printed circuit is assembled to the base as shown in FIGS. 2 and 5.

A conductor 154 extends along substrate 152. Preferably, the conductor is shaped so that, when the printed circuit 148 is assembled to the base, it overlies and follows the segment of slot 144 extending between the notches 128 and 132. The conductor may be on the underside of the substrate as shown or, more preferably, on the top thereof so that it does not contact the fluid flowing along path 20. Conductor 152 includes a first terminal extension 154a which extends laterally to and slightly beyond the outer edge of tab 152a. There is also a second end extension 154b which extends to and slightly beyond the outer edge of substrate tab 152b.

The third major component of carrier 66 is a strip 156 of metallized plastic or foil which is arranged to be adhered to the underside of plate 124 as best seen in FIG. 5. The conductive side of the strip 156 is exposed and functions (along with pad 64) as the carrier's ground plane. When the printed circuit 148 and conductive strip 156 are adhered to the top and bottom of base 122, respectively, they cover the top and bottom of the openings into the through slot 144 thus defining along with the walls of the slot, the warmer's fluid flow path 20 referred to above in connection with FIG. 2. Preferably, the strips 148 and 156 should be as thin as possible so that the conductors thereof are as close as possible to the infusate flowing through the carrier.

In order to assure a uniform cross section of flow path 20 when fluid flows through the carrier under pressure, the carriers inlet and outlet tubes 140 and 142 may comprise opposite end segments of a single tube shown in phantom at 158 in FIG. 4 laid into slot 144. When pressurized, that tube conforms generally to the walls of slot 144 between strips 148 and 156.

In use, the carrier 66 is positioned on the base section 42 of housing 40 so that the conductive side of strip 156 lies flush against the conductor pad 64 of insert 52. The only way that the carrier can be positioned thusly is when it is oriented so that the carrier's key 134 seats in the extension 58a of insert 52. When the carrier is properly seated, as shown in FIGS. 2 and 5, the overhanging ends of the carrier's terminals 154b and 154a overlie and make good electrical contact with the conductor side branches 74a and 76a, respectively, of printed circuit 72 and the conductive strip 156 is in good electrical contact with pad 64.

Preferably, the connection of the carrier conductor 154 from cable 23 via conductive stripe 74 is made at the outflow end of carrier 66 so that the warming apparatus will sense the temperatures of the infusate just as it leaves warmer 10 and enters the patient.

Also, when the carrier 66 is seated properly on base section 42, the carrier's inlet and outlet tubes 140 and 142 extend from opposite ends of base section 42. To provide clearance for these tubes when the cover section 44 is in its closed position, collinear slots 162 are provided at the ends of base section 42. Similar collinear slots 164 are also provided at the ends of the cover section 44 which, when the cover is in its closed position, mate with slots 162 to provide snug passageways for the inlet and outlet tubes 140 and 142.

To lock cover section 44 in its closed position, the cover section shell 92 is formed with an integral resilient clip 166 which extends along the forward edge of the shell. When the cover section is closed, a nose 166a extending along the lower edge of the clip is arranged to engage under a lip 168 extending along the front edge of the base section shell 52. If desired, suitable interlocks, well known in the art, may be provided to detect that carrier 66 is seated properly and cover section 44 is closed and locked before the warming apparatus will actuate.

When cover section 44 is in its closed position shown in FIG. 5, due to the resilient mounting of the cover section insert 94, the unrelieved portions of the cover section insert press down on selected areas of the carrier 66. More particularly, pad 104 engages the end segment of the carrier's flow path 20 beyond conductor terminal 154b so as to provide a relatively low impedance at that location in cavity 46. Also, the ribs 106 and 108 engage opposite sides of the carrier outboard the carrier's printed conductor 154 as well as the end of the carrier beyond the conductor terminal 154a. The gaps 110a and 110b at the opposite ends of rib 108 provide clearance for the conductor terminals 154a and 154b, respectively. The spring loaded posts 118a and 118b press down on the conductor terminals 154a and 154b, respectively, to assure that there are good electrical connections between those terminals and the pads 76a and 74a, respectively, of the printed circuit board 72.

When the illustrated warmer 10 is in operation, the fluid flow path 20 in carrier 66 conveys the infusate I from inlet fitting 12 to outlet fitting 18. The infusate flowing along that path, which has a relatively high dielectric constant, functions as the base material of a microwave integrated circuit, the housing insert 54 along with the carrier's conductive strip 156 constituting the ground plane for the cavity 46. As viewed in FIG. 5, the cavity 46 may be considered to be divided into two sections by the carrier's printed circuit 148. One cavity section 46a lying below the printed circuit is filled with the microwave-transparent carrier 66 and the infusate I in the fluid flow path 20. The other cavity section 46b above printed circuit 148 is filled with air or other material such as a low loss ceramic having a relatively low dielectric constant. Therefore, when microwave energy is coupled to the printed circuit conductor 154 by way of connector 12, a high dielectric constant exists so that substantially all of the lines of energy are concentrated in the cavity section 46a containing the infusate. Also of course, the conductive inserts 52 and 94 prevent radiation produced by the warmer from escaping from housing 40.

The infusate I flowing along the flow path 20 is highly absorbent at the microwave frequency of transmitter 26 and hence attenuates the microwave energy in the heating cavity 46. The meandering, i.e., sinuous, conductor 154 not only minimizes the length of warmer 10, but also maximizes the efficiency and power distribution of warmer 10. Preferably, the running length of conductor 154 should be long enough so that it (along with infusate I) forms a lossy transmission line which absorbs or attenuates all of the microwave energy and provides a good impedance match, and thus low reflection, within the cavity 46. As noted above, the conductive pad 104 in cover section 44 which overlies the exit end segment of flow path 20 beyond conductor 22 provides a low impedance that assures a high reflection at that end of the cavity so that any unattenuated microwave energy is reflected back into the infusate.

We have found, for example, that a warmer with a sinuous conductor 22 that is about 2¾ in. long and an amplitude of about 3/16 in. operates satisfactorily. The output end of conductor 20 (154) can either provide an open circuit or a short circuit by, respectively, not connecting or connecting printed circuit strip 76 to the ground plane, i.e., pad 64 of insert 54, either of which reflect the energy not absorbed by the infusate during the initial pass along cavity 46. Of course, if conductor 20 is open circuited, the strip 76, tab 152a and overhanging conductor segment 154a are not needed.

Referring to FIG. 2, the transmitter 26 is preferably a solid state programmable transmitter which may operate at 915 MHz and have a maximum power output of 25 watts. Such a transmitter is available from Microwave Medical Systems, Inc., Acton, Ma. That transmitter provides, if desired, short term operation with battery backup and automatic battery recharging when the unit is plugged in to an operative AC outlet. Also, detector circuits are provided in the transmitter to measure both forward and reflected power.

The radiometer 32 is also available from Microwave Medical Systems, Inc. That unit has a physical volume of about 2 cubic in. and weighs only about 3 oz. It has a center frequency of 4.0 GHz.

A diplexer 28, which is detailed in the above-identified patent application, separates the heating frequency (915 MHz.) from the radiometer frequency (4.0 GHz) which allows the use of the common coaxial cable connection to the warmer. This is very important because it minimizes the size and cost of the warming apparatus and optimizes the reliability thereof.

In use, the warmer 10 is connected in the line between the infusate source 16 and the patient P, preferably as close to the patient as practicable. Unit 26 is then electrically connected to the warmer via connector 24.

When infusate flow commences, the warming apparatus may be actuated so that transmitter 26 delivers the microwave signal to the heating cavity 46 via diplexer 28. As noted previously, the conductor 20 (154) in cavity 46 may be terminated by either an open circuit or a short circuit. In this way, any transmitter power not absorbed by the infusate I in cavity section 42 initially will be reflected back into that lossy liquid. The overall loss is enough to provide a proper impedance match to the transmitter 26.

As the infusate flowing along the flow path 20 absorbs energy, its temperature is elevated. That temperature is monitored on a non-invasive basis by the sensor 32 which, due to diplexer 28, detects only the energy associated with the temperature of the liquid being heated. The temperature-indicating signal from sensor 32 may then be processed by processor 34 and used to control transmitter 26 to maintain the infusate temperature at a selected constant value, i.e., normal body temperature, despite variations in the fluid inlet temperature and flow rate, and even at very low flow rates.

As described in the aforementioned pending application, the radiometer-type sensor 32 maybe replaced by one or more conventional thermister or thermocouple sensors positioned so that each is in contact with the infusate flowing along the flow path 20. If a single such sensor is used, it is preferably located near the exit end of the warmer so that the measured temperature is the temperature of the infusate leaving the warmer. That measurement signal may be brought out of the warmer 10 on the center conductor 23a of cable 23.

Figure 6:
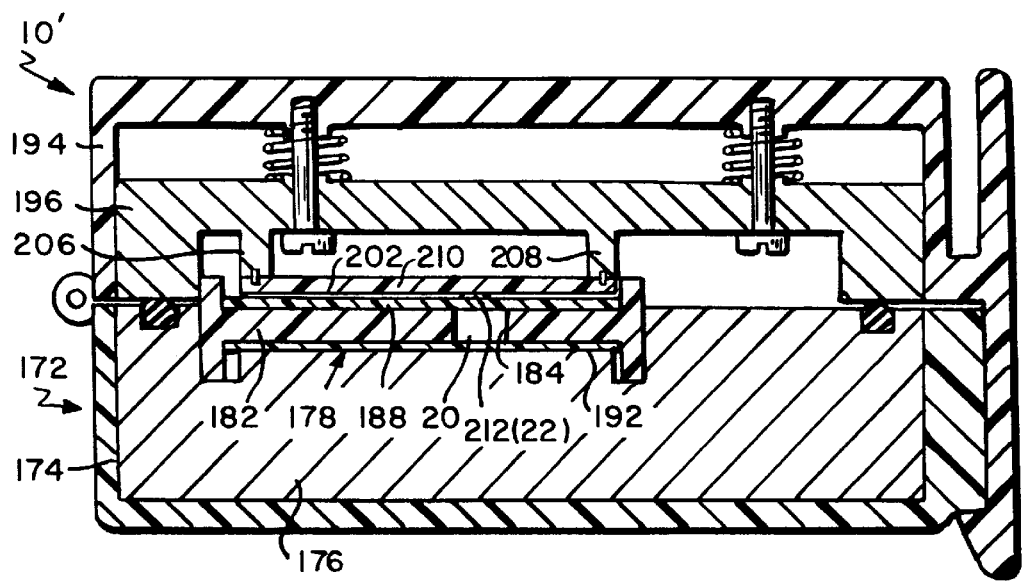
FIG. 6 is a view similar to FIG. 5 of a second warmer embodiment for use in the FIG. 1 apparatus.

To minimize the cost of carrier 66, instead of having the conductor 22 on the carrier, the conductor can be made part of the housing. FIG. 6 illustrates a warmer of this type shown generally at 10'. Warmer 10' is very similar to warmer 10 in that it has a clam shell-type housing 172 whose base section 174 may be more or less the same as section 42 described above. Base section 174 includes an insert 176 whose upper surface is shaped to accept the lower half of a fluid carrier shown generally at 178. Carrier 178 is similar to carrier 66 in that it has a rigid base 182 with a through-slot 184 whose upper and lower ends are closed by a pair of plastic strips 188 and 192, respectively. In other words, neither of those strips is conductive. The thus closed slot 184 provides the fluid flow path 20. Also, if desired, the actual flow path 20 may be further defined by a plastic tube extending along slot 184 as described above in connection with carrier 66.

Housing 172 also has a cover section 194 hinged to section 174. That cover section is similar to section 44 described above in that it has a spring-loaded insert 196 whose lower surfaces is configured to accept the upper half of carrier 178. In this embodiment, however, carrier 196 supports a printed circuit 202 such that when the cover is moved to its closed position shown in FIG. 6, the printed circuit is flush with the top of carrier 178 and presses against the upper surface of that carrier. In the illustrated embodiment, circuit 202 is supported by ribs 206 and 208 similar to ribs 106 and 108 described above.

Printed circuit 202 includes an insulating substrate 210 and a metallic stripe 212 printed on the underside of that substrate which constitutes center conductor 22. As described above, that conductor overlies the fluid flow path 20 in carrier 178 when cover section 194 is closed as in FIG. 6.

An electrical coaxial cable connection is made to one end of that conductor 22, preferably adjacent to the outflow end of warmer 10' in the same manner described in the above identified application. The opposite end of conductor 22 may be open circuited or short circuited.

When warmer 10' is in operation, microwave energy is concentrated in the lower section of the warmer's heating cavity occupied by the carrier 178 and the high dielectric constant infusate I flowing along the carrier's flow path 20. Therefore, the warmer 10' heats the infusate to a controlled temperature in a minimum amount of time in the same way, as described above in connection with warmer 10.

While FIG. 6 specifically shows the printed circuit 202 located in cover section 194, that circuit could be in base section 174. In that event, the carrier supporting pad in the base section should be of a low loss dielectric material and the metallic cover section insert 196 should be configured to press down on the entire top surface area of the carrier 178. In this way, the electromagnetic energy will be concentrated in the portion of the warmer cavity containing the infusate as described above for warmer 10'.

It will thus be seen that the objects set forth above among those made apparent from the preceding description, are efficiently attained. Also, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Infusate warming apparatus comprising
   an elongated housing having opposite ends and defining
   a heating cavity with electrically conductive interior walls;
   a divider dividing said cavity lengthwise into first and second cavity sections;
   an elongated conductor having opposite ends, said conductor extending alongside said divider in one of said cavity sections;
   fluid conducting means for conducting infusate through said first cavity section alongside said, said fluid conducting means having a fluid inlet and a fluid outlet, and
   connector means extending into said housing for coupling an external microwave signal of a selected frequency to one end of said conductor so that the conductor and infusate in said first cavity section constitute an asymmetric transmission line.

2. The apparatus defined in claim 1 wherein the conductor is affixed to said divider.

3. The apparatus defined in claim 1 wherein said fluid conducting means include a disposable fluid carrier removably positioned in said first cavity section, said carrier having a fluid inlet adjacent to one end of the housing and constituting said fluid inlet, a fluid outlet adjacent to the other end of the housing and constituting said fluid outlet and a fluid path connecting the inlet and outlet which path is adjacent to said conductor.

4. The apparatus defined in claim 3 wherein the conductor is affixed to said divider.

5. The apparatus defined in claim 3 wherein the conductor is affixed to said carrier.

6. The apparatus defined in any one of claims 3 to 5 wherein said conductor follows a meandering path alongside the divider.

7. The apparatus defined in any one of claims 3 to 5 wherein said fluid path has a footprint which is substantially the same as that of the conductor.

8. The apparatus defined in claim 1 and further including resilient means in one of said cavity sections for pressing the conductor and connector means into intimate engagement.

9. The apparatus defined in claim 1 wherein said one end of said conductor is located proximate said fluid outlet.

10. The apparatus defined in claim 1 and further including
    a microwave transmitter producing an output signal having a first frequency;
    means for coupling the transmitter to said connector means so that the signal from the transmitter provides an energy field which heats the infusate flowing through said fluid conducting means, and
    a sensor responsive to the temperature of the infusate flowing through said fluid conducting means and producing a temperature signal.

11. The apparatus defined in claim 10 wherein
    said sensor is a radiometric sensor responsive to a range of frequencies substantially higher than said first frequency, and
    said coupling means include a diplexer connecting the transmitter and sensor to said connector means.

12. The apparatus defined in claim 10 and further including processing means responsive to said temperature signal for controlling said transmitter so as to maintain the infusate at a substantially constant outlet temperature despite variations in the infusate inlet temperature and flow rate.

13. Infusate warming apparatus comprising
    a housing defining an internal cavity;
    a lossy asymmetric transmission line situated in said housing, said transmission line including an elongated electrical conductor having opposite ends and fluid conducting means for conducting infusate which is highly absorptive to electromagnetic energy of a first frequency through said housing in close proximity to the conductor, and
    connecting means extending into said housing for coupling an external electromagnetic signal of said first frequency to one end of the conductor so as to subject the infusate to an energy field which heats the infusate.

14. The apparatus defined in claim 13 and further including
    means for delivering infusate to and from said fluid conducting means;
    a transmitter producing an output signal having said first frequency, and
    coupling means for coupling said output signal to said connecting means so that the output signal produces an energy field in the housing which heats the infusate in said fluid conducting means.

15. The apparatus defined in claim 14 and further including a sensor responsive to the temperature of the infusate in said fluid conducting means and producing a temperature signal in response thereto.

16. The apparatus defined in claim 15 and further including control means responsive to the temperature signal for controlling the transmitter so as to maintain the infusate delivered from the fluid conducting means at a substantially constant temperature despite variations in the infusate inlet temperature and flow rate.

17. The apparatus defined in claim 15 wherein the sensor is a radiometric sensor responsive to a second frequency substantially higher than the first frequency, and said coupling means includes a diplexer connecting the transmitter and sensor to said connecting means.

18. The apparatus defined in claim 13 wherein said housing has electrically conductive interior walls.

19. The apparatus defined in claim 18 wherein the conductor is supported on an electrically insulating divider which divides the housing cavity lengthwise into first and second cavity sections;

the fluid conducting means includes a disposable carrier seated against the divider in one of said cavity sections, and the other of said cavity sections contains a material having a relatively low dielectric constant and which does not absorb electromagnetic energy at said first frequency.

20. The apparatus defined in claim 19 wherein the conductor follows a meandering path along the divider.

21. The apparatus defined in claim 19 wherein the carrier defines a fluid path for the infusate which substantially parallels the conductor.

22. The apparatus defined in claim 19 wherein the housing comprises two sections which are moveable relatively between an open position which allows the easy seating of the carrier against the divider and a closed position which completely encloses the carrier within the housing.

23. Infusate warming apparatus comprising a circuit board including a dielectric substrate having opposite faces and an elongated conductor extending along a face of the substrate, said conductor having first and second ends;

a housing for supporting the circuit board, said housing defining a cavity extending alongside a face of the substrate and opposite the conductor;

a low dielectric material in said cavity;

a cover hinged to the housing so that the cover can swing between an open position wherein the cover extends away from the housing and exposes the circuit board and a closed position wherein the cover covers the circuit board and forms with the housing an all around-enclosure for the circuit board, said cover having a recess to provide clearance for a fluid carrier positioned against the circuit board when the cover is moved to its closed position, and a connector extending into the housing and connected electrically to one end of the conductor.

24. The apparatus defined in claim 23 wherein the walls of the cavity and the recess are electrically conductive.

25. The apparatus defined in claim 23 and further including resilient means in the housing and/or the cover for exerting a biasing force on the circuit board.

26. The apparatus defined in claim 23 wherein the conductor faces away from the housing cavity.

27. The apparatus defined in claim 23 wherein the cavity contains air.

28. The apparatus defined in claim 23 wherein the conductor meanders along the substrate.

29. The apparatus defined in claim 23 and further including a fluid carrier positioned in the housing against the circuit board, said carrier having an inlet, an outlet and a fluid path extending between the inlet and outlet, said inlet and outlet having end portions extending out of the housing for connection to fluid lines.

30. The apparatus defined in claim 29 wherein the fluid path and the conductor are in substantial superposition.

31. The apparatus defined in claim 29 and further including interfitting means on the carrier and the housing for properly orienting the carrier when it is positioned in the housing.

32. The apparatus defined in claim 31 and further including means for preventing the cover from assuming its closed position unless the carrier is properly positioned in the housing.

33. The apparatus defined in claim 32 and further including means for locking the cover in its closed position.

34. Infusate warming apparatus comprising an elongated heating cavity having electrically conductive interior walls;

a fluid inlet into the cavity;

a fluid outlet from the cavity;

a fluid conduit for conducting a liquid through the cavity, said conduit having one end communicating with the inlet and another end communicating with the outlet;

an electrical conductor in the cavity, said conductor having first and second ends and a segment between said ends which extends alongside and generally parallel to said conduit, said conductor and the liquid in the conduit constituting a transmission line which provides a good impedance match and low reflection within the cavity so that the liquid in the conduit absorbs substantially all of the energy within the cavity, and a source for delivering an electromagnetic signal to the first end of the conductor so that the conductor radiates electromagnetic energy into the cavity, the length of the transmission line being selected so that the transmission line produces a good impedance match and low reflection within the cavity whereby the liquid in the conduit absorbs and is heated by said energy.

35. The apparatus defined in claim 34 and further including a temperature sensor for sensing the temperature of the liquid in the conduit and producing a temperature signal in response thereto.

36. The apparatus defined in claim 35 wherein the temperature sensor is located near said fluid outlet.

37. The apparatus defined in claim 35 wherein the source comprises a transmitter having a selected output signal frequency;

a receiver for receiving sensing signal, and a diplexer connected electrically between the transmitter, receiver and the first end of the conductor for coupling said output signal to the conductor and said sensor signal to the receiver while isolating said signals from each other so that the same connection to the conductor can couple said output signal to the conductor and couple the temperature signal to the receiver.

38. The apparatus defined in claim 35 wherein the sensor comprises said conductor.

39. The apparatus defined in claim 38 wherein said output signal has a first frequency, and said receiver is a radiometric receiver responsive to a range of sensor signal frequencies substantially higher than said first frequency.

40. The apparatus defined in claim 34 wherein said conductor follows a meander line.

41. The apparatus defined in claim 40 wherein the conductor is sinuous.

42. The apparatus defined in claim 40 wherein the conduit has substantially the same footprint as the conductor.

43. The apparatus defined in claim 34 wherein the second end of the conductor is short-circuited to the cavity walls.

44. The apparatus defined in claim 34 wherein the second end of the conductor is open-circuited.

45. The apparatus defined in claim 34 wherein the cavity has first and second regions;

the conductor is located in the first region and the second region is substantially filled with a material having a low dielectric constant so that the energy in the cavity is concentrated in the first region.

46. The apparatus defined in claim 45 wherein said material is air.

47. The apparatus defined in claim 34 and further including a disposable carrier for positioning in said cavity, said carrier including a rigid body having opposite sides and defining said inlet, said outlet and said conduit, said body being of a material which is substantially transparent to said energy.

48. The apparatus defined in claim 47 wherein said carrier also carries said conductor.

49. The apparatus defined in claim 47 wherein said conduit comprises a through-slot in said body;

a first strip is secured to one face of the body so as to cover the through-slot thereat, and a second strip is secured to the other face of the body to cover the through-slot thereat.

50. The apparatus defined in claim 49 wherein said first strip carries said conductor, and said second strip has an electrically conductive outer surface.

51. The apparatus defined in claim 47 and further including a circuit board positioned in said cavity so as to divide said first and second regions thereof, said conductor being printed on said circuit board.

52. The apparatus defined in claim 47 wherein said cavity is defined by a housing having first and second hinged-together sections which can close around said carrier, the first housing section along with the first face of the carrier defining the first cavity region and the second housing section along with the second face of the carrier defining the second cavity region.

53. Infusate warming apparatus comprising an elongated fluid carrier including an elongated rigid plate of low dielectric material, said plate having opposite flat faces and opposite ends;

a fluid flow path extending along the plate between said opposite ends thereof, said path having a substantially uniform cross section and a selected total length;

a fluid inlet connector at one end of the carrier and communicating with said flow path, and a fluid outlet connector at the other end of the carrier and communicating with said flow path, said inlet and outlet connectors being collinear.

54. The apparatus defined in claim 53 wherein said plate includes a through-slot extending between said faces which defines the course of said flow path between said ends, and further including first and second strips secured flush against the opposite faces of the plate so as to cover and seal the entrances into the slot thereat.

55. The apparatus defined in claim 54 and further including a flexible plastic tube extending along said slot between the opposite ends of the plate, said tube having one end communicating with said fluid inlet connector and a second end communicating with said fluid outlet connector.

56. The apparatus defined in claim 54 wherein said first and second strips are of an electrically insulating material.

57. The apparatus defined in claim 54 wherein said first strip is a printed circuit including an insulating substrate and a conductor printed on the substrate which follows the course of said flow path, and the second strip has an electrically conductive exterior surface.

58. The apparatus defined in claim 53 wherein said fluid flow path follows a meander line.

59. The apparatus defined in claim 53 wherein said carrier has longitudinal and transverse axes and is non-symmetrical about said axes so that the polarity of the carrier relative to a support can be established.

* * * * *